United States Patent [19]

Pedemonte et al.

[11] Patent Number: 5,393,884
[45] Date of Patent: Feb. 28, 1995

[54] FIBER REACTIVE ANTHRAQUINONE DYES

[75] Inventors: Ronald P. Pedemonte, Coventry; Walter Helmling, West Warwick, both of R.I.

[73] Assignee: Hoechst Celanese Corporation, Somerville, N.J.

[21] Appl. No.: 77,225

[22] Filed: Jun. 14, 1993

[51] Int. Cl.⁶ .................. C07D 251/40; C07D 251/46; C07D 251/52
[52] U.S. Cl. .................................................... 544/189
[58] Field of Search ................................. 544/187, 189

[56] References Cited

PUBLICATIONS

Niwa et al., Chemical Abstracts, vol. 98, entry 108873z (1983).
Mitsubishi Chemical., Chemical Abstracts, vol. 101, entry 56488m (1984).

Primary Examiner—John M. Ford
Attorney, Agent, or Firm—Hugh C. Crall

[57] ABSTRACT

The invention is that of a water soluble fiber reactive anthraquinone blue dyes. These dyes may be used to dye and print textiles and other substrates containing hydroxy and or groups in brilliant blue colors. The dyes of the invention are free of heavy metals.

8 Claims, No Drawings

FIBER REACTIVE ANTHRAQUINONE DYES

BACKGROUND OF THE INVENTION

1. Technical Field

This invention relates to the field of anthraquinone, fiber-reactive dyes.

2. Background

The present invention is directed to water-soluble, fiber-reactive anthraquinone dyes. The class of anthraquinone dyes is well known in the art. Anthraquinone dyes are generally considered to possess good dye properties. However, as a class they suffer from the disadvantage of high raw material cost. It is therefore important in the industrial dyeing and printing of substrates for a dye to provide superior dye properties, and superior processing characteristics at a competitive cost.

U.S. Pat. No. 5,112,971 represents an attempt to produce improved anthraquinone dyes having fiber reactive moieties useful in dyeing or printing substrates containing hydroxyl and/or amide groups. The dyes of this prior art reference may be represented by the following formula:

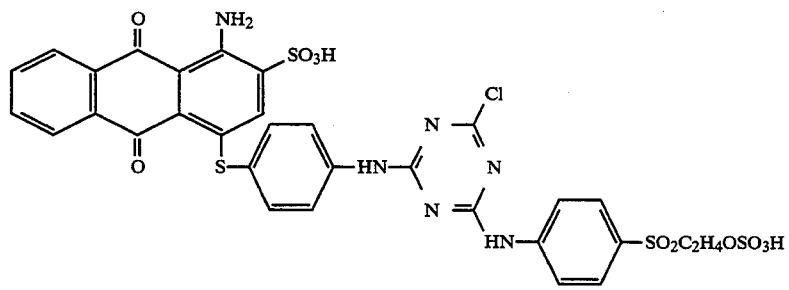

The novel dyes of this invention provide dyed or printed substrates with excellent fastness properties including chlorine, light and was fastness. In addition, the dyes of the invention are easily synthesized. Another advantage is that the dyes of the invention provide brilliant blue shades without metal complexing the dye; i.e. they are free of heavy metals.

SUMMARY OF THE INVENTION

This invention is that of a new fiber reactive dyes of the formula:

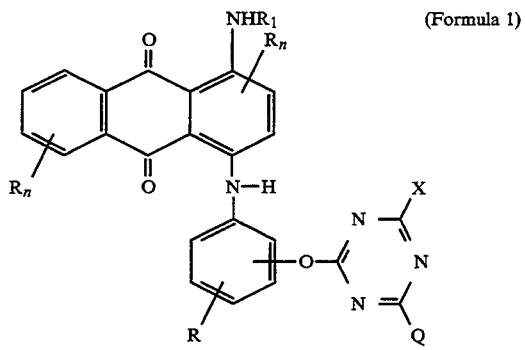
(Formula 1)

wherein:

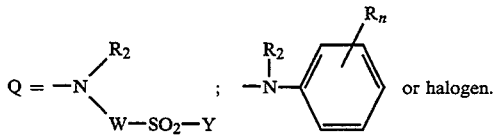

W is a direct covalent bond, a substituted or unsubstituted arylene, or alkylene, or arylene-alkylene group wherein the alkylene group may be interrupted by a hetero atom selected from O,S and N;

R is independently selected from hydrogen, $C_1$-$C_6$ alkyl;

$C_1$-$C_6$ alkoxy, sulfo and carboxy;

$R_1$ is selected from hydrogen, $C_1$-$C_6$ alkyl and phenyl;

$R_2$ and $R_3$ are independently selected from hydrogen substituted or unsubstituted $C_1$-$C_6$ alkyl and —W-$SO_2Y$;

n is an integer of 1 or 2;

X is F, Cl, $NR_2R_3$, NHCN, OH or Q; and

Y is CH=$CH_2$, or $CH_2CH_2Z$ wherein Z is a group capable of being split off by the action of an alkali reagent.

The dyes of the invention are free of heavy metals. They provide dyeings and prints in brilliant blue shades having excellent fastness properties and they are easily synthesized. The dyes of the invention may be applied by methods well known in the art for dyeing and printing textiles and other substrates.

DESCRIPTION OF THE PREFERRED EMBODIMENTS

The fiber reactive, water soluble dyes of this invention are anthraquinone dyes which may be represented by the following general formula:

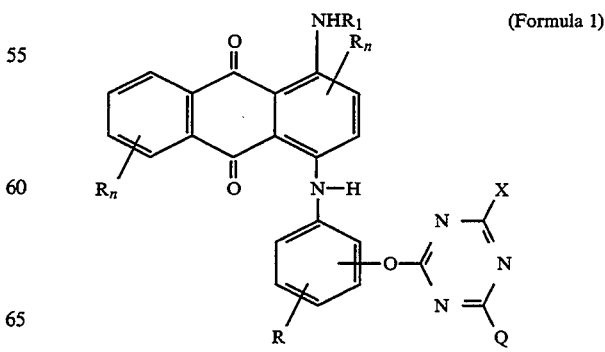
(Formula 1)

wherein:

-continued

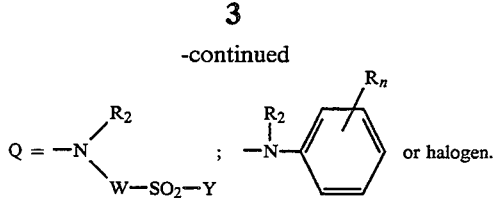

W is independently selected from a direct covalent bond, a substituted or unsubstituted arylene, or alkylene, or arylene- alkylene group wherein the alkylene group may be interrupted by a hetero atom selected from O,S and N, preferably a substituted or unsubstituted phenylene or naphthylene group or a substituted or unsubstituted $C_1$ to $C_6$ alkylene group, wherein said alkylene moiety may be interrupted by a hetero atom selected from O,N and S;

R is independently selected from hydrogen, a substituted or unsubstituted $C_1$-$C_6$ alkyl; a substituted or unsubstituted $C_1$-$C_6$ alkoxy, sulfo and carboxy;

$R_1$ is selected from hydrogen, $C_1$-$C_6$ alkyl and phenyl;

$R_2$ and $R_3$ are independently selected from hydrogen, substituted and unsubstituted $C_1$-$C_6$ alkyl and —W—$SO_2$Y;

n is an integer of 1 or 2;

X is selected from F, Cl, $NR_2R_3$, NHCN, OH or Q; and

Y represents a fiber reactive group which is selected from CH=$CH_2$ and $CH_2CH_2$—Z wherein Z represents an organic or inorganic moiety which may be split off by treatment with an alkali reagent. Z is preferably selected from —Cl, —Br, —$OSO_3H$, —$SSO_3H$, —$OPO_3H_2$; most preferably Z is the sulfato group.

The term "arylene-alkylene" group as used in this specification and the claims is intended to mean a phenylene or naphthylene group bonded to one or more alkylene groups, e.g. the following illustrations or their isomers:

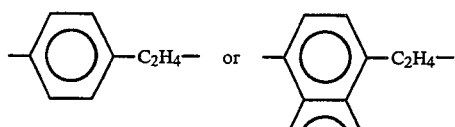

or

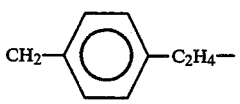

Examples of R, $R_1$ and $R_2$ are: hydrogen or $CH_3$, $C_2H_5$, n-$C_3$—$H_7$, n-$C_4H_9$, n-$C_6H_3$, which may be optionally substituted by OH, $OCH_3$, $OC_2H_5$, COOH, $SO_3H$, $OSO_3H$, CN, Cl, or F.

Examples of the substituents in substituted $C_1$-$C_6$ -alkyl and $C_1$-$C_6$ -alkoxy, groups are OH, $OCH_3$, $OC_2H_5$, COOH, $SO_3H$, $OSO_3H$, CN, Cl, Br or F; preferably $OCH_3$, $OC_2H_5$ and $OSO_3H$.

Examples of the substituents in substituted phenyl, phenylene or naphthylene groups are Cl, Br, $CH_3$, $C_2H_5$, $OCH_3$, $SO_3H$, COOH and $OC_2H_5$.

Preferably R and $R_1$ are hydrogen; $R_2$ and $R_3$ are preferably hydrogen, $CH_3$ or $C_2H_5$; W is preferably phenylene or naphthalene which may be substituted by methyl, methoxy, carboxy and sulfo. Y is preferably vinyl or sulfatoethyl, X is preferably F, Cl, NHCN, $HNR_2$ and OH and n is preferably 1.

The anthraquinone dyes of the invention may be prepared using methods known in the art; see for example U.S. Pat. No. 5,112,971 (issued May 12, 1992) which discloses a process for preparing anthraquinone dyes. Anthraquinone compounds of the following general Formula 2 are known as is their methods of preparation. They are the basic raw material for the anthraquinone chromophore.

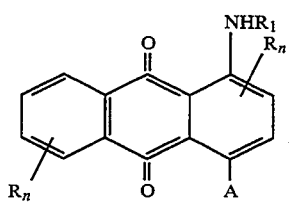

(Formula 2)

wherein R, $R_1$ and n are as previously defined and A is a leaving group such as halogen (Cl, F, Br, I), nitro, sulfo and the like; preferably A is halogen.

Compounds of Formula 2 may be reacted according to Ullmann condensation reaction with a substituted or unsubstituted aminophenol of the following formula:

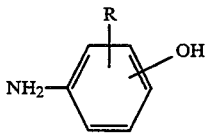

(Formula 3)

wherein R is defined above.

The resulting condensate may be represented by the following general Formula 4:

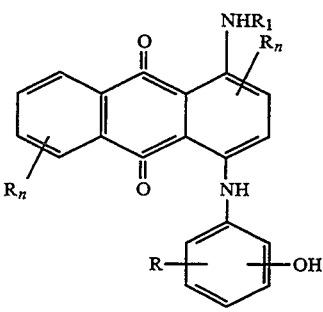

(Formula 4)

The chromophore represented by Formula 4 is condensed with the condensation product of a chlorotriazine compound of the following Formula

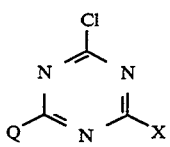

(Formula 5)

wherein Q and X are defined above.

The subsequent condensation product of the chlorotriazine compound of Formula 5 with the chromophore of Formula 4 may be represented by the following formula (Formula 6):

(Formula 6)

In the event Q is a halogen, it may be replaced by the moiety:

$$-N\begin{array}{c}R_2\\W-SO_2Y\end{array}$$

This compound of Formula 6 when Q is halogen is then condensed with a substituted amine of the following general Formula 7:

$$H-N\begin{array}{c}R_2\\W-SO_2Y\end{array}$$ (Formula 7)

wherein $R_2$, W and Y are defined above.

It will be apparent to the skilled worker that the order of reaction may be modified, for example, the substituted amine of Formula 7 may be reacted with the chlorotriazine compound of Formula 5 and the resulting addition product may be condensed with the compound of Formula 4. In addition, it would be obvious for the skilled worker to first condense the compound of Formula 4 with chlorotriazine followed by the sequential addition of the moiety X and then the substituted amine of Formula 7. It will also be apparent to the skilled worker that the reaction mixture may be a mixture of fiber reactive moieties and depending on the reaction conditions e.g. up to 30% of the vinyl moiety and up to about 5% of the non-reactive hydroxy moiety may be formed.

Exemplary anthraquinones of Formula 2 are:
1-amino-2,4-dibromoanthraquinone;
1-amino-2-bromo-4-nitroanthraquinone;
1-cyclohexylamino-4-bromoanthraquinone;
1-benzoylamino-4-bromoanthraquinone;
1-isopropylamino-2-carboxy-4-bromoanthraquinone;
1-cyclohexylamino-4-bromoanthraquinone-5-, 6-, 7- or 8-sulfonic acid;
1-amino-4-bromoanthraquinone-2-sulfonic acid;
1-amino-4-bromoanthraquinone-2,6- or 2,7-disulfonic acid;
1-amino-4-bromoanthraquinone-2,5,8-trisulfonic acid;
1-methylamino-4-bromoanthraquinone-2-sulfonic acid;
1-ethylamino-4-bromoanthraquinone-2-sulfonic acid;
1-propylamino-4-bromoanthraquinone-2-sulfonic acid;
1-amino-4-bromoanthraquinone-2-carboxylic acid;
1-amino-4-bromoanthraquinone-2-sulfonic acid-6-carboxylic acid;
1-amino-4-bromoanthraquinone-2-sulfonic acid-7-carboxylic acid and the like.

Exemplary aminophenols of Formula 3:
4-aminophenol;
2-aminophenol;
3-aminophenol;
2-hydroxy-5-aminobenzenesulfonic acid;
2-amino-5-hydroxybenzenesulfonic acid;
2-hydroxy-4-aminobenzenesulfonic acid;
4-aminosalicyclic acid;
5-aminosalicyclic acid;
2-amino-4-methylphenol;
4-amino-2-methylphenol;
4-amino-3-methylphenol; and
5-amino-2-methoxyphenol.

Exemplary type "Q" groups are: 2-($\beta$-Sulfatoethylsulfonyl)-phenyl-amino, 3-($\beta$-Sulfatoethylsulfonyl)-phenyl-amino, 4-($\beta$-Sulfatoethylsulfonyl)-phenyl-amino, 2-Carboxy-5-)$\beta$-sulfatoethylsulfonyl)-phenyl-amino, 2-Chloro-3-($\beta$-Sulfatoethylsulfonyl)-phenyl-amino, 2-Chloro-4-($\beta$-sulfatoethylsulfonyl)-phenyl-amino, 2-Ethoxy-4- or 5-($\beta$-sulfatoethylsulfonyl)-phenyl-amino, 2-Ethyl-4-($\beta$-sulfatoethylsulfonyl)-phenyl-amino, 2-Methoxy-5-($\beta$-sulfatoethylsulfonyl)-phenyl-amino, 2,3-Dimethoxy-5-($\beta$-sulfatoethylsulfonyl)-phenyl-amino, 2,4-Dimethoxy-5-($\beta$-sulfatoethylsulfonyl)-phenyl-amino, 2,5-Dimethoxy-4-($\beta$-sulfatoethylsulfonyl)-phenyl-amino, 2-Methoxy-5-methyl-4-(6-sulfatoethylsulfonyl)-phenyl-amino, 2- or 3- or 4-($\beta$-Thiosulfatoethylsulfonyl)-phenyl-amino, 2-Methoxy-5-($\beta$-thiosulfatoethylsulfonyl)-phenyl-amino, 2-Sulfo-4-($\beta$-phosphatoethylsulfonyl)-phenyl-amino, 2-Sulfo-4-vinylsulfonyl-phenyl-amino, 2-Hydroxy-4- or-5-($\beta$-sulfatoethylsulfonyl)-phenyl-amino, 2-Chloro-4- or-5-($\beta$-chloroethylsulfonyl)-phenyl-amino, 2-Hydroxy-3-sulfo-5-($\beta$-sulfatoethylsulfonyl)-phenyl-amino, 3- or 4-($\beta$-Acetoxyethylsulfonyl)-phenyl-amino, 2-Methoxy-4-[$\beta$-(N-methyl-tauryl)-ethylsulfonyl]-phenyl-amino, 5-($\beta$-Sulfatoethylsulfonyl)naphth-2-yl-amino, 6- or 7- or 8-($\beta$-Sulfatoethylsulfonyl)-naphth-2-yl-amino, 6-($\beta$-Sulfatoethylsulfonyl)-1-sulfo-naphth-2-yl-amino, 5-($\beta$-Sulfatoethylsulfonyl)-1-sulfo-naphth-2-yl-amino, 8-($\beta$-Sulfatoethylsulfonyl)-6-sulfo-naphth-2-yl-amino, $\beta$-[4-($\beta$-Sulfatoethylsulfonyl)phen]-ethylamino, $\beta$-[2-Sulfo-4-($\beta$-sulfatoethylsulfonyl)-phen]-ethylamino, $\beta$-($\beta'$-Chloroethylsulfonyl)-ethylamino, $\beta$-($\beta$-Sulfatoethylsulfonyl)-ethylamino, $\beta$-(Vinylsulfonyl)-ethylamino, $\gamma$-($\beta'$Chloroethylsulfonyl)-propylamino, $\gamma$-($\beta'$-Sulfatoethylsulfonyl)-propylamino, $\gamma$-($\beta'$-Bromoethylsulfonyl)-propylamino, $\gamma$-(Vinylsulfonyl)-propylamino, 1-Methyl-1-($\beta$-sulfatoethylsulfonyl)-1-ethylamino, $\delta$-($\beta'$-Sulfatoethylsulfonyl)-butylamino, 2-Methyl-2-($\beta$-chloroethylsulfonyl)-1-propylamino, $\omega$-($\beta'$-Chloroethylsulfonyl)-pentylamino, $\beta$-($\beta'$Chloroethylsulfonyl)-n-hexylamino, N-Methyl-N-[$\beta$-($\beta'$chloroethylsulfonyl)-ethyl]-amino, N-Ethyl-N-[$\beta$-($\beta$-chloroethylsulfonyl)-ethyl] -amino, N-n-Propyl-N-[$\beta$-($\beta'$chloroethylsulfonyl)-ethyl]-amino, N-Carboxymethyl-N-[$\beta$-($\beta'$-bromoethylsulfonyl)-ethyl]-amino, N-Sulfatomethyl-N-[$\beta$-($\beta'$-chloroethylsulfonyl)-ethyl]-amino, N-($\beta$-Carboxyethyl)-N-[$\gamma'$-($\beta$-chloroethylsulfonyl)-propyl]-amino-N-($\beta$-Sulfatoethyl)-N-[$\gamma'$-($\beta''$-chloroethylsulfonyl)-propyl]-amino, N-($\beta$-Sulfatoethyl)-N-[$\delta'$-($\beta''$chloroethylsulfonyl)-butyl]-amino, N-($\beta$-Ethoxyethyl)-N-[$\delta'$-($\beta''$-chloroethylsulfonyl)-butyl]-amino, N-($\gamma$-Chloropropyl)-N-[$\beta'$-($\beta''$-chloroethylsulfonyl)- ethyl]-amino, N-Phenyl-N-[β-(β'chloroethylsulfonyl)-ethyl]-amino, N-(3-Sulfophenyl)-N-[β-(β'-chloroethylsulfonyl)-ethyl]-amino, N-(4-Sulfophenyl)-N-[β-(β'-chloroethylsulfonyl)-ethyl]-amino, Bis-[β-(β'-chloroethylsulfonyl)-ethyl]-amino, Bis-[β-(β'-bromoethylsulfonyl)-ethyl]-amino, Bis-[γ-(β'-chloroethylsulfonyl)-propyl]-amino, Bis-[δ-(β'-chloroethylsulfonyl)-butyl]-amino, Bis-(β-vinylsulfonyl-ethyl)-amino, N-(β-Cyanoethyl)-N-[γ'-(β''-chloroethyisulfonyl)-propyl]-amino, β-[β'-(β'''-Chloroethylsulfonyl)-ethylamino]-ethylamino, β-[β'(β''-Sulfatoethylsulfonyl)-ethylamino]-ethylamino, β-[β'(β''-Chloroethylsulfonyl)-ethoxy]-ethylamino, β-[β'-(β''-Sulfatoethylsulfonyl)-ethoxy]-ethylamino, 3,4-Di-(β-sulfatoethylsulfonyl)-phenylamino, 2,5 Disulfo-phenylamino,N-Ethyl-phenylamino, N-Ethyl-[4-(β-sulfato-ethylsulfonyl) phenyl]-amino, N-Methyl-[3-(β-sulfato-ethylsulfonyl) phenyl]-amino,
2,5-Di(β-sulfatoethylsulfonyl)-phenylamino,
4-[γ-(β'Sulfatoethylsulfonyl)-propoxy]-phenylamino,
2,5-Bis-[(β-sulfatoethylsulfonyl)-methyl],phenylamino,
N-Methyl-N-[4-(β-sulfatoethylsulfonyl)-phenyl]-amino,
N-Methyl-N-[3-(β-sulfatoethylsulfonyl)-phenyl]-amino,
N-Ethyl-N-[4-(β-sulfatoethylsulfonyl)-phenyl]-amino,
Phenylamino,
N-Ethyl-N-[3-(β-sulfatoethylsulfonyl)-phenyl]-amino,
and halogen (chloro, fluoro and bromo).

The amino moieties (Q) are obtained from the corresponding amines e.g.:
2-5-Disulfo-aniline;
2-(β-Sulfatoethylsulfonyl)-aniline;
3-(β-Sulfatoethylsulfonyl)-aniline;
4-(β-Sulfatoethylsulfonyl)-aniline;
2-Carboxy-5-(β-sulfatoethylsulfonyl)-aniline;
2-Chloro-3-(β-Sulfatoethylsulfonyl)-aniline;
2-Chloro-4-(β-sulfatoethylsulfonyl)-aniline;
2-Ethoxy-4- or 5-(β-sulfatoethylsulfonyl)-aniline;
2-Ethyl-4-(β-sulfatoethylsulfonyl)-aniline;
2-Methoxy-5-(β-sulfatoethylsulfonyl)-aniline;
2,3-Dimethoxy-5-(β-sulfatoethylsulfonyl)-aniline;
2,4-Dimethoxy-5-(β-sulfatoethylsulfonyl)-aniline;
2,5-Dimethoxy-4-(β-sulfatoethylsulfonyl)-aniline;
2-Methoxy-5-methyl-4-(β-sulfatoethylsulfonyl)-aniline;
2- or 3- or 4-(β-thiosulfatoethylsulfonyl)-aniline;
2- Methoxy-5-(β-thiosulfatoethylsulfonyl)-aniline;
2-Sulfo-4-(β-phosphatoethyisulfonyl)-aniline;
2-Sulfo-4-vinylsulfonyl-aniline;
2-Hydroxy-4- or 5-(β-sulfatoethylsulfonyl)-aniline;
2-Chloro-4- or -5-(β-chloroethylsulfonyl)aniline;
3,4-Di-(β-sulfatoethylsulfonyl)-aniline;
2,5-Di(β-sulfatoethylsulfonyl)-aniline;
2,5-Bis-[(β-sulfatoethylsulfonyl)-methyl]aniline;
N-Methyl-N-[4-(β-sulfatoethylsulfonyl)]aniline;
N-Methyl-N-[3-(β-sulfatoethylsulfonyl)]aniline;
N-Ethyl-N-[4-(β-sulfatoethylsulfonyl)]aniline;
N-Ethyl-N-[3-(β-sulfatoethylsulfonyl)]aniline; and
1-phenylaminoethane-2-sulfonic acid.

After preparation, the dyes may be isolated as a powder, either by salting out of solution or by spray drying, and brought to standard strength by the addition of inorganic salt, generally sodium sulfate. Advantageously, the prepared dyestuff may be used directly as a liquid composition after standardizing with water. Such liquid compositions will contain from 5 to 45% (by weight) of the dyes of the invention.

The dyes of the invention in this description are shown in their free acid form. They may be employed in their free acid form or as salts of the acid. Preferably, they are used in their salt form and in particular as the alkali metal and alkaline earth metal salts; e.g. as sodium, potassium, lithium and the like.

The dyes of the invention may be employed to dye materials such as cotton, linen, viscose, rayon, wool, silk and synthetic polyamides by methods well known in the art e.g. exhaust dyeing methods such beck, jet, and package dyeing or continuous pad dyeing techniques.

The following examples illustrate the invention but are not intended to limit its scope unless otherwise specified. In the examples and the claims, percentages and parts are by weight and temperatures are ° C.

EXAMPLE 1

A dye of the following formula was made:

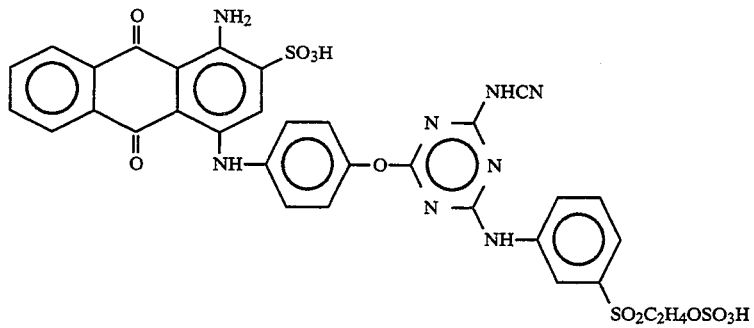

1.3 parts of cyanamide and 5.6 parts of cyanuric chloride were condensed at 0°-5° C. in an aqueous medium of pH 8.5-9.5. The product was condensed with 15.3 parts of 1-amino-4-[(4-hydroxyanilino)]-9,10-dioxo-2-anthracenesulfonic acid at 10°-30° C. and at a pH of 8-10. This second product was condensed with 8.5 parts of 1-aminobenzene-3-(2-sulfatoethyl)sulfone at 40°-50° C. and at a pH of 3.5-4.0. The product was isolated by salting out with 20 parts of sodium chloride followed by filtration to afford 24 parts of a greenish blue dye having an absorbance of 0.350 at a lambda max of 603 nm and an assay of 79% by HPLC.

EXAMPLE 2:

A dye of the following formula was made:

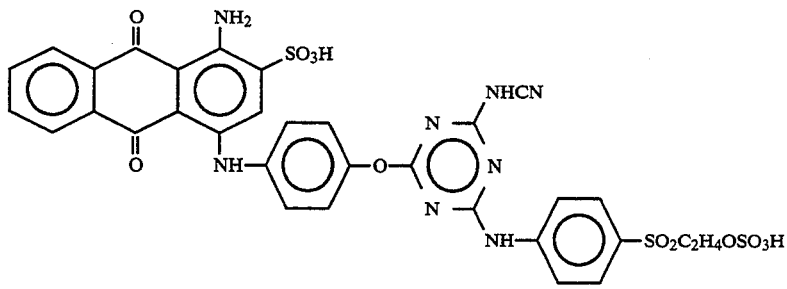

This compound was prepared by the above procedure substituting 1-aminobenzene-4-(2-sulfatoethyl)sulfone for 1-aminobenzene-3-(2sulfatoethyl)sulfone. The product was a greenish blue dye having an absorbance of 0.300 at a lambda max of 603 nm and an assay of 70% by HPLC.

Similar dyes may be prepared using the foregoing procedures. These dyes have the following general formula and are illustrated below:

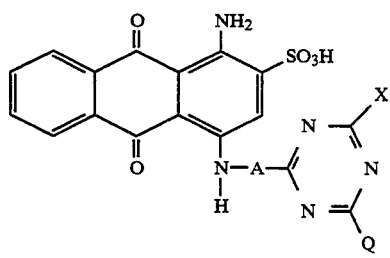

wherein: X is F, Cl, NHCN, OH or $NR_2R_3$.

| EXAMPLE # | A | Q |
|---|---|---|
| 8 | 4-C6H4-O- | NH-(2-OCH3,5-SO2CH2CH2OSO3H)C6H3 |
| 9 | 4-C6H4-O- | NH-(2-OCH3,5-CH3,4-SO2CH2CH2OSO3H)C6H2 |
| 10 | 4-C6H4-O- | NH-(2-OCH3,5-OCH3,4-SO2CH2CH2OSO3H)C6H2 |
| 11 | 4-C6H4-O- | N(CH3)-(4-SO2CH2CH2OSO3H)C6H4 |
| 12 | 3-C6H4-O- | NH-(4-SO2CH2CH2OSO3H)C6H4 |
| 13 | 3-C6H4-O- | NH-(3-SO2CH2CH2OSO3H)C6H4 |
| 14 | 3-C6H4-O- | NH-(2-OCH3,5-SO2CH2CH2OSO3H)C6H3 |
| 15 | 2-C6H4-O- | NH-(2-OCH3,5-SO2CH2CH2OSO3H)C6H3 |
| 16 | 2-C6H4-O- | NH-(2-OCH3,5-CH3,4-SO2CH2CH2OSO3H)C6H2 |
| 17 | 2-C6H4-O- | N(CH3)-(4-SO2CH2CH2OSO3H)C6H4 |
| 18 | 4-C6H4-O- | NH-(4-SO2CH2CH2OSO3H)C6H4 |
| 19 | 4-C6H4-O- | NH-(2-OCH3,5-SO2CH2CH2OSO3H)C6H3 |
| 20 | 4-C6H4-O- | N(CH3)-(4-SO2CH2CH2OSO3H)C6H4 |
| 21 | 4-C6H4-O- | NH-(2-OCH3,5-CH3,4-SO2CH2CH2OSO3H)C6H2 |

-continued

| EX-AMPLE # | A | Q |
|---|---|---|
| 22 | 4-methyl-2-hydroxyphenyl-SO3H (via O) | 4-(SO2CH2CH2OSO3H)phenyl-NH |
| 23 | 4-methyl-2-hydroxyphenyl-SO3H (via O) | 3-(SO2CH2CH2OSO3H)phenyl-NH |
| 24 | 4-methyl-2-hydroxyphenyl-SO3H (via O) | 2-OCH3-5-(SO2CH2CH2OSO3H)phenyl-NH |
| 25 | 4-methyl-2-hydroxyphenyl-SO3H (via O) | 4-(SO2CH2CH2OSO3H)phenyl-NCH3 |
| 26 | 4-methyl-2-sulfophenyl (via O) | 4-(SO2CH2CH2OSO3H)phenyl-NH |
| 27 | 4-methyl-2-sulfophenyl (via O) | 3-(SO2CH2CH2OSO3H)phenyl-NH |
| 28 | 4-methyl-2-sulfophenyl (via O) | 2-OCH3-5-(SO2CH2CH2OSO3H)phenyl-NH |
| 29 | 4-methyl-2-sulfophenyl (via O) | 2-OCH3-4-CH3-5-(SO2CH2CH2OSO3H)phenyl-NH |
| 30 | 4-methyl-2-sulfophenyl (via O) | 4-(SO2CH2CH2OSO3H)phenyl-NCH3 |

Additional dyes may be prepared using the foregoing procedures. These dyes have the following general formula and are illustrated below:

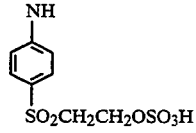

wherein: X is F, Cl, NHCN, OH or NR2R3.

| EX-AMPLE # | A | Q |
|---|---|---|
| 31 | 4-methylphenyl (via O) | 2-OCH3-phenyl-NH with SO2CH2CH2OSO3H |
| 32 | 4-methylphenyl (via O) | 2-OCH3-5-CH3-4-(SO2CH2CH2OSO3H)phenyl-NH |
| 33 | 4-methylphenyl (via O) | 2-OCH3-5-OCH3-4-(SO2CH2CH2OSO3H)phenyl-NH |
| 34 | 4-methylphenyl (via O) | 4-(SO2CH2CH2OSO3H)phenyl-NCH3 |
| 35 | 3-methylphenyl (via O) | 4-(SO2CH2CH2OSO3H)phenyl-NH |
| 36 | 3-methylphenyl (via O) | 3-(SO2CH2CH2OSO3H)phenyl-NH |
| 37 | 3-methylphenyl (via O) | 2-OCH3-5-(SO2CH2CH2OSO3H)phenyl-NH |
| 38 | 2-methylphenyl (via O) | 2-OCH3-5-(SO2CH2CH2OSO3H)phenyl-NH |
| 39 | 2-methylphenyl (via O) | 2-OCH3-4-CH3-5-(SO2CH2CH2OSO3H)phenyl-NH |

Similarly, dyes may be prepared using the foregoing procedures. These dyes have the following general formula and are illustrated below:
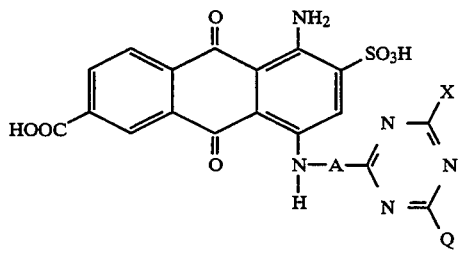
wherein: X is F, Cl, NHCN, OH or NR₂R₃.

-continued

| EX-AMPLE # | A | Q |
|---|---|---|
| 59 | —⌬—O— | NH, OCH₃, SO₂CH₂CH₂OSO₃H (phenyl) |
| 60 | —⌬—O— | NCH₃, SO₂CH₂CH₂OSO₃H (phenyl) |
| 61 | —⌬—O— | NH, OCH₃, CH₃, SO₂CH₂CH₂OSO₃H (phenyl) |
| 62 | O—⌬—SO₃H | NH, SO₂CH₂CH₂OSO₃H (phenyl) |
| 63 | O—⌬—SO₃H | NH, SO₂CH₂CH₂OSO₃H (phenyl) |
| 64 | O—⌬—SO₃H | NH, OCH₃, SO₂CH₂CH₂OSO₃H (phenyl) |

EXAMPLE 65

Example 8 may be repeated wherein the moiety Q is:

$$-\overset{H}{N}-CH_2-CH_2-CH_2-SO_2-CH=CH_2$$

EXAMPLE 66

Example 8 may be repeated wherein the moiety Q is:

$$-N(CH_2-CH_2-SO_2CH=CH_2)_2$$

EXAMPLE 67

Example 8 may be repeated wherein the moiety Q is:

$$-\overset{H}{N}-CH_2-CH_2-O-CH_2-CH_2-SO_2-CH=CH_2$$

EXAMPLE 68

Example 8 may be repeated wherein the moiety Q is:

$$-N[CH_2-CH_2-CH_2-SO_2-CH_2-CH_2-Cl]_2$$

EXAMPLE 69

Example 8 may be repeated wherein the moiety Q is:

$$-N[CH_2-CH_2-CH_2-SO_2-CH=CH_2]_2$$

Similarly, dyes may be prepared using the foregoing procedures. These dyes have the following general formula and are illustrated below:

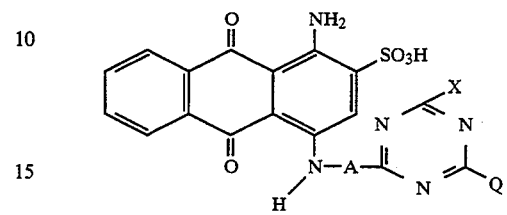

wherein: X is F.

| EXAMPLE # | A | Q |
|---|---|---|
| 70 | —⌬—O— | —NH—phenyl |
| 71 | —⌬—O— | —NH—phenyl(SO₃H)(SO₃H) |
| 72 | —⌬—O— | —N(C₂H₅)—phenyl |
| 73 | —⌬—O— | —NH—phenyl |
| 74 | —⌬—O— | —N(C₂H₄SO₃H)—phenyl |

Similarly, dyes may be prepared using the foregoing procedures. These dyes have the following general formula and are illustrated below:

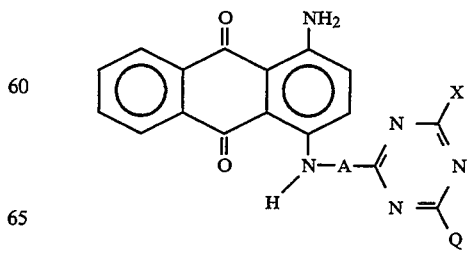

wherein: X is Cl.

| EX-AMPLE # | A | Q |
|---|---|---|
| 75 | —⌬—O | —N(C₂H₅)—⌬—SO₂CH₂CH₂OSO₃H |
| 76 | —⌬—O | —N(C₂H₅)—⌬(SO₂CH₂CH₂OSO₃H) |

Similarly, dyes may be prepared using the foregoing procedures. These dyes have the following general formula and are illustrated below:

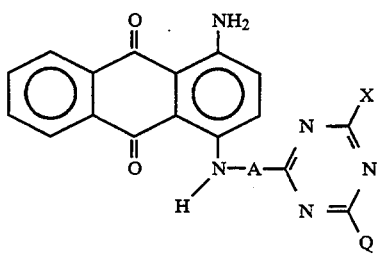

wherein: X is Cl.

| EXAMPLE # | A | Q |
|---|---|---|
| 77 | ⌬—O | —N(C₂H₅)—⌬—SO₂CH₂CH₂OSO₃H |
| 78 | ⌬—O | —N(C₂H₅)—⌬(SO₂CH₂CH₂OSO₃H) |

Similarly, dyes may be prepared using the foregoing procedures. These dyes have the following general formula and are illustrated below:

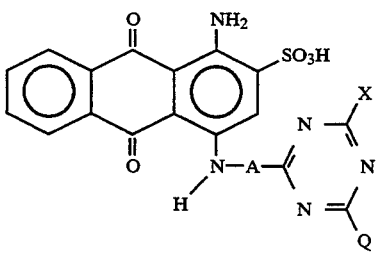

wherein: X is Q.

| EX-AMPLE # | A | Q |
|---|---|---|
| 79 | —⌬—O | —NH—⌬—SO₂CH₂CH₂OSO₃H |
| 80 | —⌬—O | —NH—⌬(SO₂CH₂CH₂OSO₃H) |
| 81 | ⌬—O | —NH—⌬—SO₂CH₂CH₂OSO₃H |
| 82 | ⌬—O | —NH—⌬(SO₂CH₂CH₂OSO₃H) |

The invention may be embodied in other specific forms without departing from the spirit or essential characteristics thereof. Through this specification and the appended claims, a given chemical name or formula is intended to encompass all isomers of said name or formula where such isomers exist. The present embodiments are therefore to be considered in all respects as illustrative and not restrictive, the scope of the invention being indicated by the appended claims rather than by the foregoing description; and all changes which come within the meaning and equivalency of the claims are therefore intended to be embraced therein.

We claim:

1. A compound of the formula:

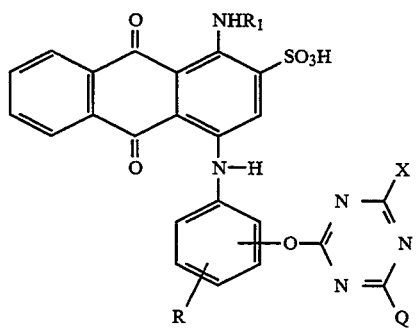

wherein:

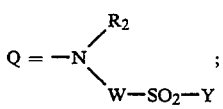

W is independently selected from a direct covalent bond, an arylene selected from phenylene and naphthalene, or a $C_1$ to $C_6$ alkylene, or arylene-alkylene group wherein the alkylene group may be interrupted by a hetero atom selected from O, S and N;

wherein said arylene moiety may be optionally substituted with Cl, Br, $CH_3$, $C_2H_5$, $OCH_3$, $SO_3H$, COOH and $OC_2H_5$ R is independently selected from hydrogen, a $C_1$ to $C_6$ alkyl; a $C_1$ to $C_6$ alkoxy; sulfo and carboxy;

$R_1$ is selected from hydrogen, $C_1$ to $C_6$ alkyl and phenyl;

$R_2$ and $R_3$ are independently selected from hydrogen, a $C_1$ to $C_6$ alkyl and —$WSO_2Y$;

n is an integer of 1 or 2;

X is F, Cl, HNCH, $NR_2R_3$, OH or Q; and

Y represents a fiber reactive group which is selected from $CH=CH_2$ and $CH_2CH_2$—Z wherein Z is selected from the group consisting of Cl, Br, OSO$_3$H, SSO$_3$H and OPO$_3$H$_3$.

2. A compound according to claim 1 wherein W is a C$_1$ to C$_6$ alkylene group wherein said alkylene group may be interrupted by a hetero atom selected from O, S and N.

3. A compound according to claim 1 wherein X is selected from F,Cl, NHR$_2$; NHCN and OH wherein R$_2$ is selected from hydrogen or a C$_1$ to C$_6$ alkyl and Y is selected from Cl, Br, OSO$_3$H and OPO$_3$H$_2$.

4. A compound according to claim 3 wherein X is selected from F and Cl and Q is:

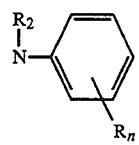

wherein R and R$_2$ are independently selected from C$_1$ to C$_6$ alkyl and sulfo, and n is 1 or 2.

5. A compound according to claim 3 for the following formula:

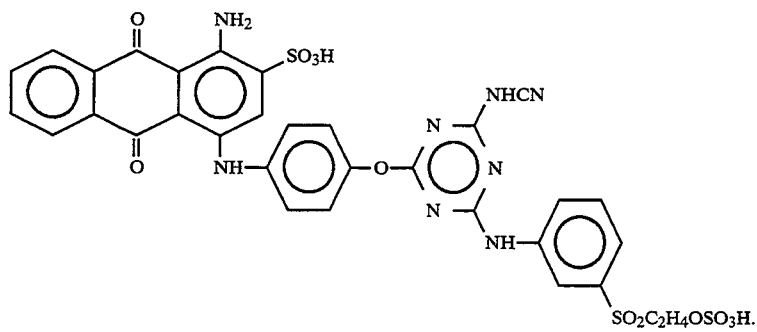

6. A compound according to claim 3 of the following formula:

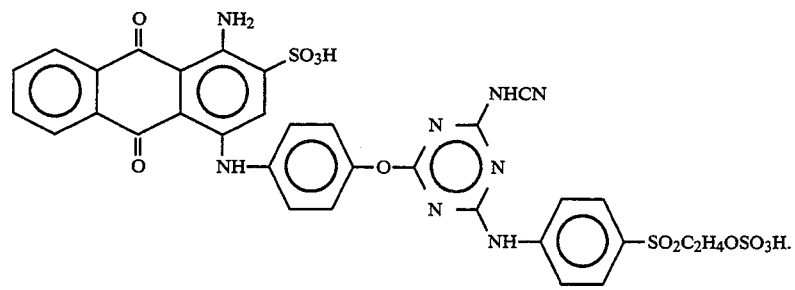

7. A compound according to claim 3 of the following formula:

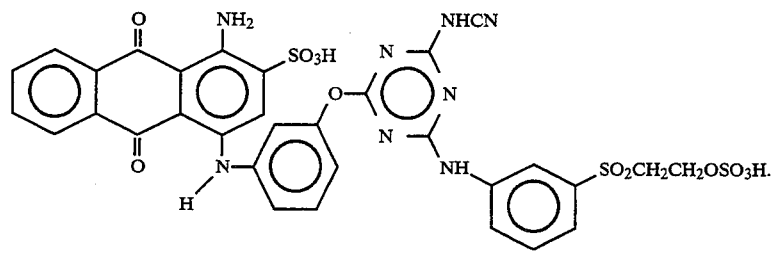

8. A compound according to claim 3 of the following formula:

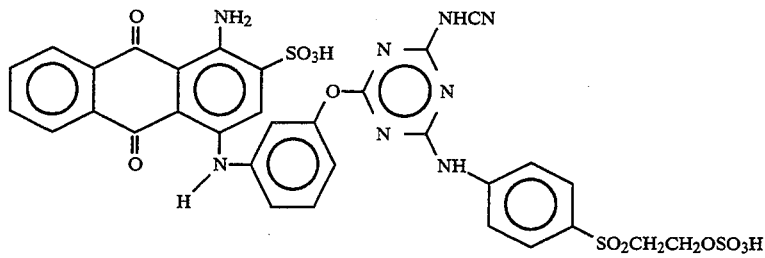

* * * * *